(12) United States Patent
Fenske et al.

(10) Patent No.: US 8,009,033 B2
(45) Date of Patent: *Aug. 30, 2011

(54) SYSTEM AND METHOD FOR PROVIDING SYNERGISTIC ALERT CONDITION PROCESSING IN AN AUTOMATED PATIENT MANAGEMENT SYSTEM

(75) Inventors: Matthew Fenske, Glen Ellyn, IL (US); Benjamin L. Somberg, Shoreview, MN (US); Jeffrey E. Stahmann, Ramsey, MN (US); Mark L. Cohen, Atlanta, GA (US); Dale E. Foster, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,283

(22) Filed: Jan. 4, 2011

(65) Prior Publication Data
US 2011/0106555 A1    May 5, 2011

Related U.S. Application Data

(63) Continuation of application No. 12/651,536, filed on Jan. 4, 2010, now Pat. No. 7,884,709, which is a continuation of application No. 11/447,743, filed on Jun. 5, 2006, now Pat. No. 7,649,449.

(51) Int. Cl.
*G08B 29/00* (2006.01)
(52) U.S. Cl. .................. 340/506; 340/539.12; 340/573.1
(58) Field of Classification Search ............... 340/539.1, 340/539.12, 506, 500, 573.1; 705/1–3; 600/300, 600/301
See application file for complete search history.

(56) References Cited

U.S. PATENT DOCUMENTS

| | | | |
|---|---|---|---|
| 5,355,889 | A | 10/1994 | Nevo et al. |
| 5,576,952 | A | 11/1996 | Stutman et al. |
| 5,942,986 | A | 8/1999 | Shabot et al. |
| 6,171,237 | B1 | 1/2001 | Avitall et al. |
| 6,336,903 | B1 | 1/2002 | Bardy |
| 6,368,284 | B1 | 4/2002 | Bardy |
| 6,398,728 | B1 | 6/2002 | Bardy |
| 6,411,840 | B1 | 6/2002 | Bardy |
| 6,416,471 | B1 | 7/2002 | Kumar et al. |
| 6,440,066 | B1 | 8/2002 | Bardy |
| 7,117,028 | B2 | 10/2006 | Bardy |
| 7,238,156 | B1 | 7/2007 | Adamczyk |
| 7,256,708 | B2 | 8/2007 | Rosenfeld et al. |

(Continued)

OTHER PUBLICATIONS

Partial File History for co-pending U.S. Appl. No. 11/121,593 "System and Method for Managing Coordination of Collected Patient Data in an Automated Patient Management System," (219 pages).

(Continued)

*Primary Examiner* — Eric M Blount
(74) *Attorney, Agent, or Firm* — Pauly, Devries, Smith & Deffner, L.L.C.

(57) ABSTRACT

A system and method for providing synergistic alert condition processing in an automated patient management system is presented. An alert condition is classified along a continuum that includes adverse outcome potential versus medical intervention impact potential. The alert condition is managed by assigning a disposition based on relative placement of the alert condition along the continuum. An alert notification is communicated over a selectable mode of communications and is conditioned upon the assigned disposition being actionable.

19 Claims, 8 Drawing Sheets

U.S. PATENT DOCUMENTS

| | | |
|---|---|---|
| 7,307,543 B2 | 12/2007 | Rosenfeld et al. |
| 7,395,216 B2 | 7/2008 | Rosenfeld et al. |
| 7,399,276 B1 | 7/2008 | Brown et al. |
| 7,468,032 B2 | 12/2008 | Stahmann et al. |
| 2002/0169584 A1* | 11/2002 | Fu et al. ................ 702/188 |
| 2004/0103001 A1 | 5/2004 | Mazar et al. |
| 2004/0122294 A1 | 6/2004 | Hatlestad et al. |
| 2004/0122296 A1 | 6/2004 | Hatlestad et al. |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0249250 A1 | 12/2004 | McGee et al. |
| 2006/0047538 A1 | 3/2006 | Condurso et al. |
| 2006/0253300 A1 | 11/2006 | Somberg et al. |
| 2006/0253301 A1 | 11/2006 | Simms et al. |

OTHER PUBLICATIONS

Partial File History for co-pending U.S. Appl. No. 11/121,594 "System and Method for Managing Patient Triage in an Automated Patient Management System," (161 pages).

Partial File History for co-pending U.S. Appl. No. 11/121,870 "System and Method for Managing Alert Notifications in an Automated Patient Management System," (200 pages).

Health Insurance Portability and Accountability Act of 1996, Pub. L. No. 104-191, 110 Stat. 1936 (1996).

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

Security and Electronics Signature Standards, 63 Fed. Reg. 155 (proposed Aug. 12, 1998).

* cited by examiner

SYSTEM AND METHOD FOR PROVIDING SYNERGISTIC ALERT CONDITION PROCESSING IN AN AUTOMATED PATIENT MANAGEMENT SYSTEM

This application is a continuation of co-pending U.S. application Ser. No. 12/651,536, filed Jan. 4, 2010, which is a continuation of U.S. application Ser. No. 11/447,743, filed Jun. 5, 2006 (now U.S. Pat. No. 7,649,449, issued Jan. 19, 2010), herein incorporated by reference.

FIELD OF THE INVENTION

The invention relates in general to automated patient management and, specifically, to a system and method for providing synergistic alert condition processing in an automated patient management system.

BACKGROUND OF THE INVENTION

The efficient and effective delivery of health care has been substantially improved through the development of newer and better ways of measuring patient parameters and managing patient information. Modern clinical practice frequently makes use of equipment and devices that measure such global parameters as blood pressure, blood-gas levels, temperature, cardiac function, and so forth. Other specialized devices, such as implantable medical devices (IMDs) and drug-delivery devices, automatically control and monitor various physiological functions in accordance with predetermined treatment protocols tailored to the needs of particular patients. Still other devices have been developed to periodically check in with patients and, for example, remind them to take prescriptions, visit their doctors, or otherwise take appropriate therapeutic action. Reliance on such devices frees health care professionals to attend to the needs of other patients and focus their attention on those matters where direct human intervention is still required. Reliance on such devices also improves patient well-being and quality of life by freeing the patients from the need for constant direct care by health professionals.

One adverse consequence of such progress is the problem of how best to manage the disparate and voluminous data often generated by the equipment and devices now available. The modern-day problem of "information overload" is as prevalent and serious in the field of automated remote health care as elsewhere. A need exists not only for better ways of obtaining relevant information regarding patients and their conditions, but for managing and making best use of that information once obtained.

To manage the multitude of data now made available to health care professionals in the course of medical treatment, various systems and methods have been proposed and developed. Conventional patient monitors, for example, sound a warning in the event a measured parameter, such as cardiac activity, falls outside of pre-determined limits. Other devices, such as implantable pacemakers or automatic defibrillators, are programmed to implement therapeutic protocols automatically in the event that certain physiological conditions are detected. Still other devices have been developed to remind patients when to take a prescription or otherwise implement a predetermined treatment protocol. Although effective for their particular functions, such approaches have been largely independent of one another and lack a centralized coordinating facility that consolidates widely disparate data into a cohesive and meaningful whole.

Therefore, a need exists for frequent and near continuous monitoring of patients with implanted and external medical devices and sensors for problems occurring with their device, sensor outputs, and overall health status. For example, an individual parameter that may not, by itself, indicate a problem might well indicate a problem when combined with information from one or more additional sources. In the past, resolving this problem has required substantial involvement and intervention of health care personnel who can interpret the data and take action as appropriate. In the case of patients who might face potentially critical situations, prudence requires the patients remain in health care facilities, even though their actual condition would permit life outside such a facility.

SUMMARY OF THE INVENTION

A system and method includes continuously processing alert conditions originating from a source providing device parameters, sensor readings, health conditions, or similar data. Each alert condition is analyzed and classified into groupings, as indicated along a continuum that relates potential adverse outcome to potential impact from medical intervention. In a further embodiment, combined alert conditions are formed from two or more non-alert conditions that may be actionable or alert conditions of non-actionable magnitude. The alert conditions are managed through a plurality of states, which include disposition, severity, prioritization, and escalation. Finally, each alert condition is journaled into an electronic medical records system database and, as appropriate, communicated as an alert notification to a patient, physician, or third party.

One embodiment provides a system and method for providing synergistic alert condition processing in an automated patient management system. An alert condition is classified along a continuum that includes adverse outcome potential versus medical intervention impact potential. The alert condition is managed by assigning a disposition based on relative placement of the alert condition along the continuum. An alert notification is communicated over a selectable mode of communications and is conditioned upon the assigned disposition being actionable.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Automated Patient Management Environment

Figure 1:
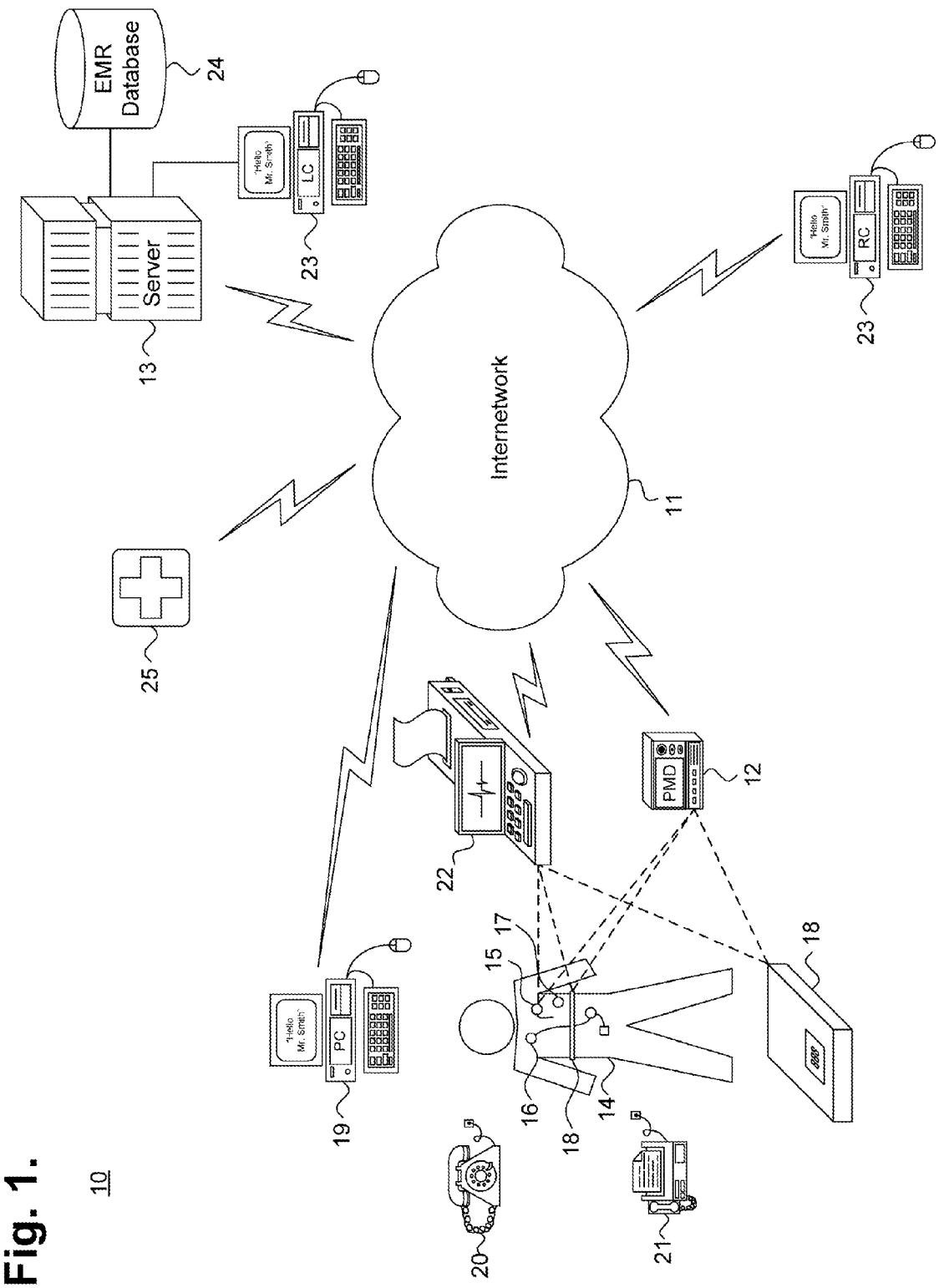
FIG. 1 is a functional block diagram showing, by way of example, an automated patient management environment.

Automated patient management encompasses a range of activities, including remote patient management and automatic diagnosis of patient health, such as described in commonly-assigned U.S. Patent application Pub. No. US2004/0103001, published May 27, 2004, pending, the disclosure of which is incorporated by reference. Such activities can be performed proximal to a patient, such as in the patient's home or office, centrally through a centralized server, such from a hospital, clinic or physician's office, or through a remote workstation, such as a secure wireless mobile computing device. FIG. 1 is a functional block diagram showing, by way of example, an automated patient management environment 10. In one embodiment, a patient 14 is proximal to one or more patient monitoring or communications devices, which are interconnected remotely to a centralized server 13 over an internetwork 11, such as the Internet, or through a public telephone exchange (not shown), such as a conventional or mobile telephone network. The patient monitoring or communications devices non-exclusively include a patient management device 12, such as a repeater, personal computer 19, including a secure wireless mobile computing device, telephone 20, including a conventional or mobile telephone, and facsimile machine 21. In a further embodiment, a programmer 22, such as a programmer or programmer-recorder, can be used by clinicians, such as physicians, nurses, or qualified medical specialists, to interrogate and program medical devices. Finally, the centralized server 13 is remotely interfaced to a patient care facility 25, such as a clinic or hospital, to ensure access to medical response or patient care providers. Other patient monitoring or communications devices are possible. In addition, the internetwork 11 can provide both conventional wired and wireless interconnectivity. In one embodiment, the internetwork 11 is based on the Transmission Control Protocol/Internet Protocol (TCP/IP) network communication specification, although other types or combination of networking implementations are possible. Similarly, other network topologies and arrangements are possible.

Each patient management device 12 is uniquely assigned to a particular patient 14 to provide a localized and network-accessible interface to one or more medical devices, which serve as patient data sources 15-18, either through direct means, such as wired connectivity, or through indirect means, such as induction or selective radio frequency or wireless telemetry based on, for example, "strong" Bluetooth or IEEE 802.11 wireless fidelity "WiFi" interfacing standards. Other configurations and combinations of patient data source interfacing are possible.

Patient data includes physiological measures, which can be quantitative or qualitative, parametric data regarding the status and operational characteristics of the patient data source itself, and environmental parameters, such as the temperature or time of day. Other types of patient data are possible. The patient data sources collect and forward the patient data either as a primary or supplemental function. Patient data sources 15-18 include, by way of example, medical therapy devices that deliver or provide therapy to the patient 14, medical sensors that sense physiological data in relation to the patient 14, and measurement devices that measure environmental parameters occurring independent of the patient 14. Each patient data source can generate one or more types of patient data and can incorporate one or more components for delivering therapy, sensing physiological data, measuring environmental parameters, or a combination of functionality. In a further embodiment, data values can be entered by a patient 14 directly into a patient data source. For example, answers to health questions could be input into a measurement device that includes interactive user interfacing means, such as a keyboard and display or microphone and speaker. Such patient-provided data values could also be collected as patient information. Additionally, measurement devices are frequently incorporated into medical therapy devices and medical sensors. Medical therapy devices include implantable medical devices (IMDs) 15, such as pacemakers, implantable cardiac defibrillators (ICDs), drug pumps, and neuro-stimulators, and external medical devices (EMDs) 16, such as automatic external defibrillators (AEDs) and continuous positive airway pressure (CPAP) machines. Medical sensors include implantable sensors 17, such as implantable heart and respiratory monitors and implantable diagnostic multi-sensor non-therapeutic devices, and external sensors 18, such as Holter monitors, weight scales, blood oxygen saturation sensors, and blood pressure cuffs. Other types of medical therapy, medical sensing, and measuring devices, both implantable and external, are possible.

The patient management device 12 collects and temporarily stores patient data from the patient data sources 15-18 for periodic upload over the internetwork 11 to the server 13 and storage in an electronic medical records (EMR) database 24.

Each patient data source 15-18 collects the quantitative physiological measures on a substantially continuous or scheduled basis and also records the occurrence of events, such as therapy or irregular readings. In a still further embodiment, the patient management device 12, personal computer 19, telephone 20, or facsimile machine 21 record or communicate qualitative quality of life (QOL) measures or symptom assessments that reflect the subjective impression of physical well-being perceived by the patient 14 at a particular time. Other types of patient data collection, periodicity and storage are possible.

In a further embodiment, the collected patient data can also be accessed and analyzed by one or more clients 23, either locally-configured or remotely-interconnected over the internetwork 11. The clients 23 can be used, for example, by clinicians to securely access stored patient data assembled in the database 21 and to select and prioritize patients for health care provisioning, such as respectively described in commonly-assigned U.S. patent application Ser. No. 11/121,593, filed May 3, 2005, pending, and U.S. patent application Ser. No. 11/121,594, filed May 3, 2005, pending, the disclosures of which are incorporated by reference. Although described herein with reference to physicians or clinicians, the entire discussion applies equally to organizations, including hospitals, clinics, and laboratories, and other individuals or interests, such as researchers, scientists, universities, and governmental agencies, seeking access to the patient data.

The collected patient data can also be evaluated for the occurrence of one or more conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

Figure 2:
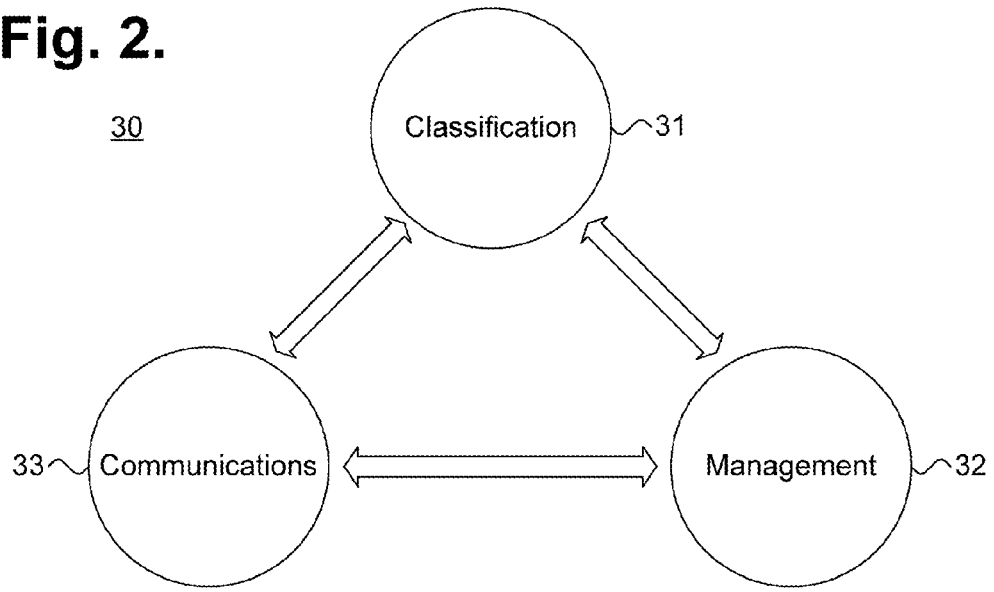
FIG. 2 is a process flow diagram showing synergistic alert condition processing in the automated patient management environment of FIG. 1.

Finally, alert conditions occurring in the collected patient data can potentially trigger one or more alert notifications that provide external indicators of the alert condition occurrences, as further described below beginning with reference to FIG. 2. Alert notification can be defined to be performed in either the server 13, patient collection device 12, or one or more other devices either operating as part of or as adjunct to the internetwork 11, such as described in commonly-assigned U.S. patent application Ser. No. 11/121,870, filed May 3, 2005, pending, the disclosure of which is incorporated by reference.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the server 13 is a server-grade computing platform configured as a uni-, multi- or distributed processing system, and the clients 23 are general-purpose computing workstations, such as a personal desktop or notebook computer. In addition, the patient management device 12, server 13 and clients 23 are programmable computing devices that respectively execute software programs and include components conventionally found in computing device, such as, for example, a central processing unit (CPU), memory, network interface, persistent storage, and various components for interconnecting these components.

Synergistic Alert Condition Processing

Alert conditions originate from sources providing device parameters, sensor readings, health conditions, and similar data. Alert condition sources non-exclusively include implantable medical devices 15, external medical devices 16, implantable sensors 17, external sensors 18, patient management devices 12, personal computers 19, telephones 20, facsimile machines 21, and any other devices capable of reliably collecting or receiving quantitative or qualitative patient health information.

Alert conditions need to be processed in a timely and efficient manner. FIG. 2 is a process flow diagram showing synergistic alert condition processing 30 in the automated patient management environment 10 of FIG. 1. Each alert condition is processed through three stages 31-33. First, classification 31 includes receiving, analyzing, and classifying each alert condition based on originating source as indicated along a continuum that relates potential adverse outcome to potential impact from medical intervention, as further described below with reference to FIG. 7. Second, management 32 includes determining the appropriate disposition of each alert condition and can also include applying thresholds, determining severity, and prioritizing between multiple competing alert conditions, as further described below with reference to FIG. 8. Finally, communications 33 includes journaling each alert condition into the EMR database 24 and sending an alert notification, if appropriate, as further described below with reference to FIG. 9. Journaling may also include the storage of contextual information temporally surrounding the alert, such as patient activity, heart rate, blood pressure, or any other data from alert condition sources 15-21. Other alert condition processing stages are possible.

Adverse Outcomes Versus Physician Interventions

Figure 3:
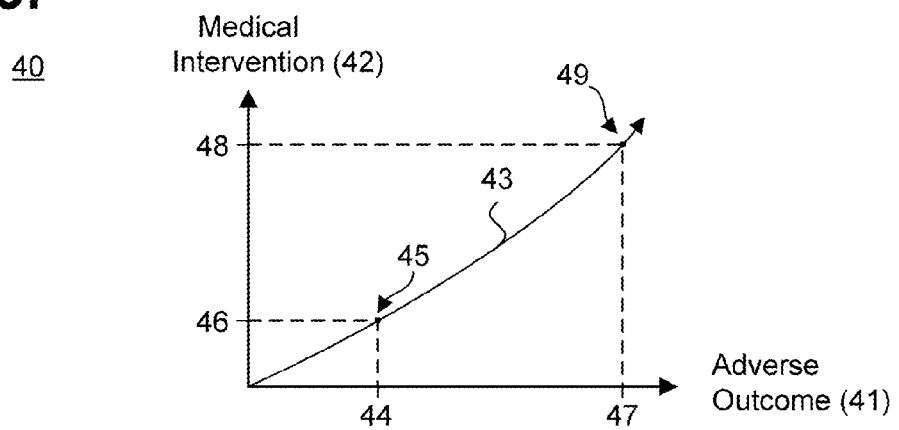
FIG. 3 is a graph diagram showing, by way of example, adverse outcomes versus medical interventions.

Alert conditions are classified along a continuum of two scales that map a relationship between potential adverse outcome and potential impact from medical intervention. FIG. 3 is a graph 40 showing, by way of example, adverse outcomes versus medical interventions. The x-axis 41 represents the potential for an adverse outcome that could potentially result from health concerns causing or underlying the alert condition. The y-axis 42 represents the potential impact resulting from medical intervention.

The relationship between adverse outcome 41 and medical intervention 42 is provided as a continuum 43. Placement of an alert condition along the continuum 43 reflects the overall urgency of the alert condition, which can also be associated with a particular mode of communication with a physician, patient, or third party, as appropriate. For example, point 45 indicates a low potential for an adverse outcome 44 and commensurately low potential impact from medical intervention 46. Accordingly, point 45 could be associated with an informational message that could be sent to a physician. In comparison, point 49 indicates a high potential impact for an adverse outcome 47 and a commensurately high potential for impact from medical intervention 48. Accordingly, point 49 could be associated with a medical emergency notification that would be sent to the patient, physician, and third parties, such as medical emergency response personnel. Other forms and shapes of continuums are possible, as well as types of associated alert notifications, and communication modes, which could be customized based on the preferences of the physician, patient, and third parties.

Non-Alert Conditions

Figure 4:
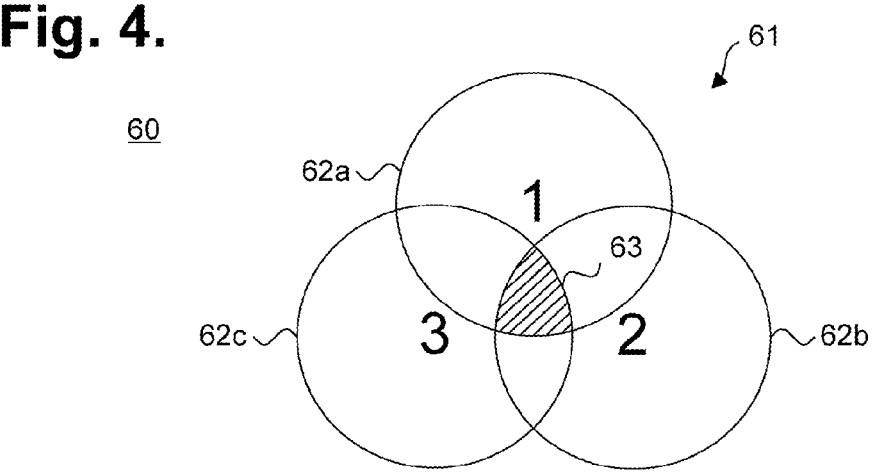
FIG. 4 is a Venn diagram showing, by way of example, a confluence of a set of non-alert conditions in the automated patient management environment of FIG. 1.

In addition to the continuum 43 mapping the relationship between adverse outcome potential and medical intervention impact potential, other conditions either amounting to nominal alert conditions that may be actionable or non-alert conditions can, in combination, nevertheless, qualify as bona fide alert conditions when viewed in combination. FIG. 4 is a Venn diagram 60 showing, by way of example, a confluence 63 of a set of non-alert conditions 62a-c in the automated patient management environment 10 of FIG. 1. Each non-alert condition 62a-c either fails to qualify as a true alert condition or is, at best, an alert condition of nominal magnitude with non-actionable potential adverse outcome. When taken in combination 61, the confluence 63 of the individual non-alert conditions 62a-c signify a combined alert condition that indicates a strong potential for adverse outcome with correspondingly strong potential impact from medical intervention.

The individual non-alert conditions 62a-c can be defined for individual patients or groups of patients sharing common physiological conditions, clinical trajectories, medical histories, and so forth. For example, a moderate decrease in lead impedance coupled with a moderate decrease in R-wave amplitude with a slight increase in threshold could constitute an insulation break not normally identifiable by inspecting any of the parameters independently. Other types of relationships and combinations of non-alert conditions and alert conditions with non-actionable potential adverse outcomes are possible.

Alert Condition Management States

Figure 5:
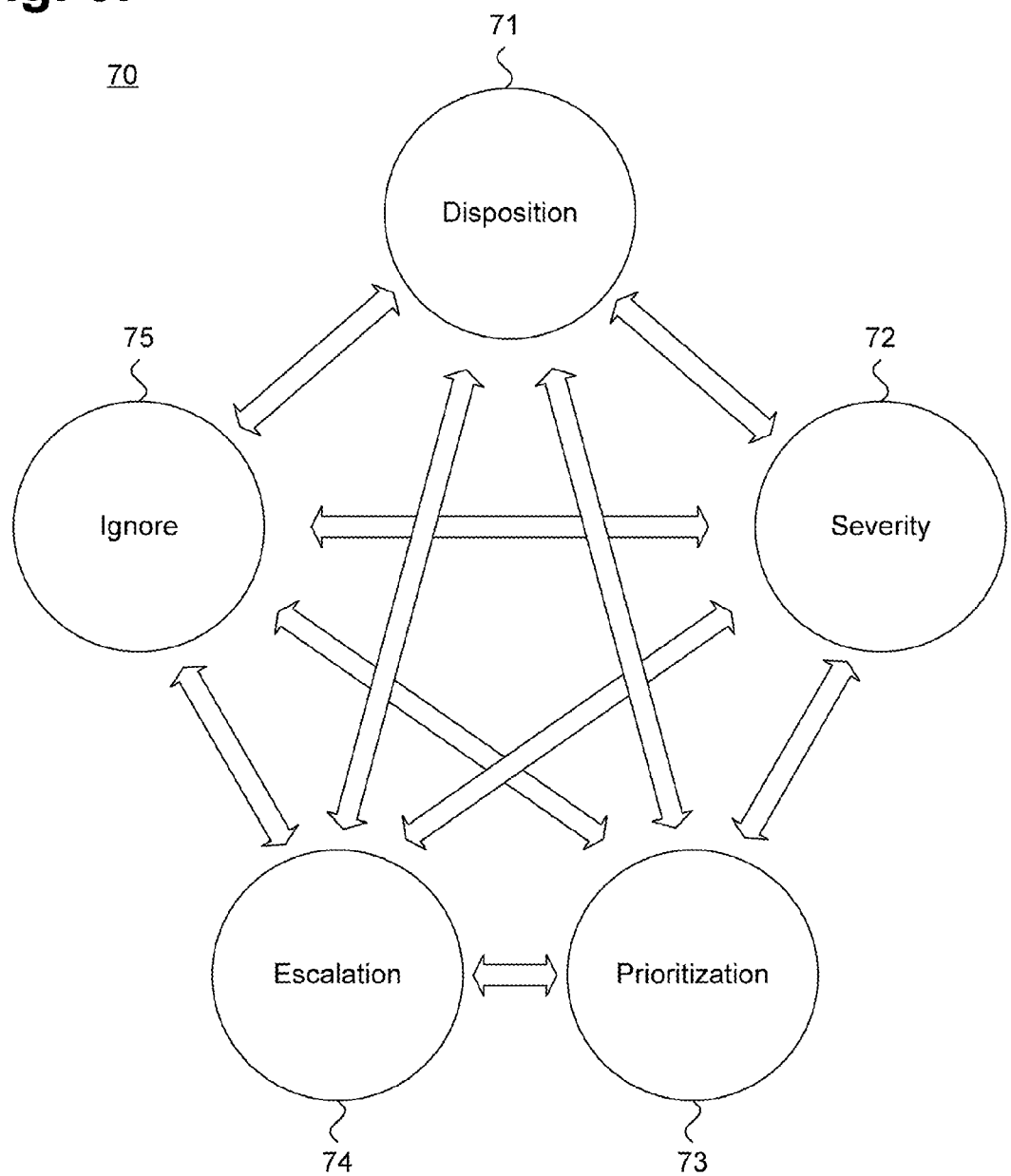
FIG. 5 is a data flow diagram showing alert condition management states for use in the automated patient management environment of FIG. 1.

Primarily, managing alert conditions requires determining an appropriate disposition, but can also include determining a severity level or priority, or whether to escalate the alert condition. FIG. 5 is a data flow diagram 70 showing alert condition management states 71 for use in the automated patient management environment 10 of FIG. 1. In one embodiment, alert conditions are managed through five states that include disposition 71, severity 72, prioritization 73, escalation 74, and ignoring the alert condition 75. Other alert condition management states are possible.

Disposition 71 involves selecting the appropriate action, if any, to take on an alert condition. Ignoring 75 an alert condition is a form of disposition that requires no action be taken, whereas an actionable disposition includes, in order of increasing involvement, recording the alert condition in the EMR database 24; sending an informational message to the patient, physician or third party; sending a recommendation to the patient, physician or third party; sending an obligatory instruction to the patient, physician or third party; and taking active medical interventive measures, such as reprogramming an implantable medical device 15. Other dispositions are possible.

Severity 72 assigns alert conditions or combined alert conditions into ad hoc groupings that can be associated with particular dispositions 71 or priorities 73. Severity levels can include labels, such as color coding, for instance, red, yellow, amber, and so forth, for each grouping to aid in understanding and usage. Severity 72 is tied to prioritization 73 and escalation 74, which respectively ranks multiple competing alert conditions and promotes actionable alert conditions that remain ignored or unaddressed. Prioritization 73 implements a form of triage that factors in health condition types, health condition severities, and available facilities. Escalation 74 provides a mechanism to increase the level of medical intervention for an actionable alert condition that has remained unaddressed or acknowledged for a pre-determined time period. Other alert condition management states 71 are possible.

Method

Figure 6:
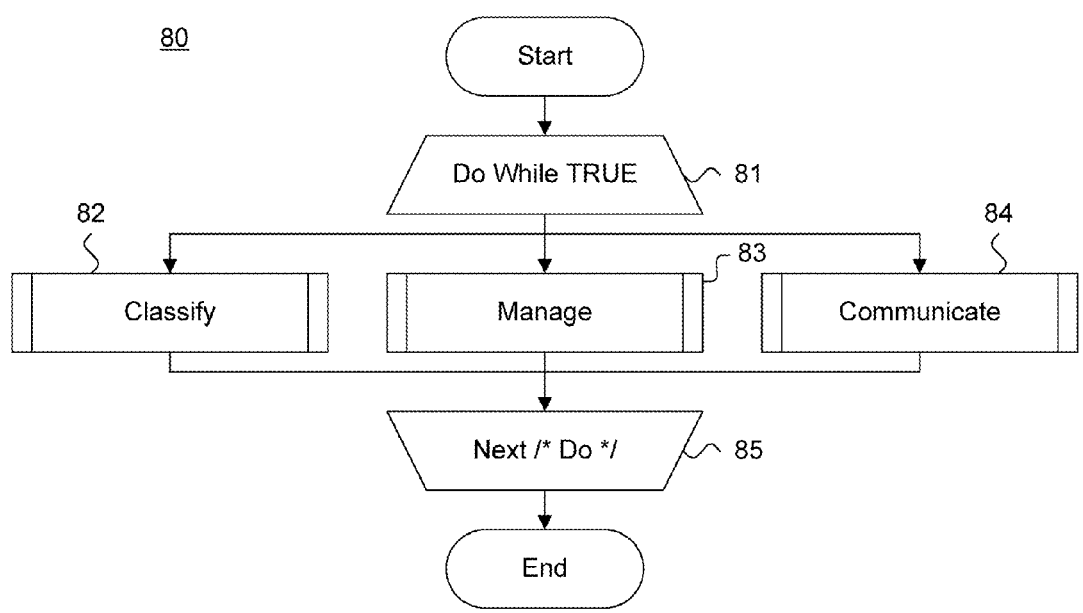
FIG. 6 is a flow diagram showing a method for providing synergistic alert condition processing in an automated patient management system, in accordance with one embodiment.

Alert condition processing is performed continuously by cycling through each alert condition source and generating alert notifications, as appropriate. FIG. 6 is a flow diagram showing a method 80 for providing synergistic alert condition processing in an automated patient management system 10, in accordance with one embodiment. Generally, the method 80 proceeds by processing alert conditions in a continuous cycle (block 81-85).

Figure 7:
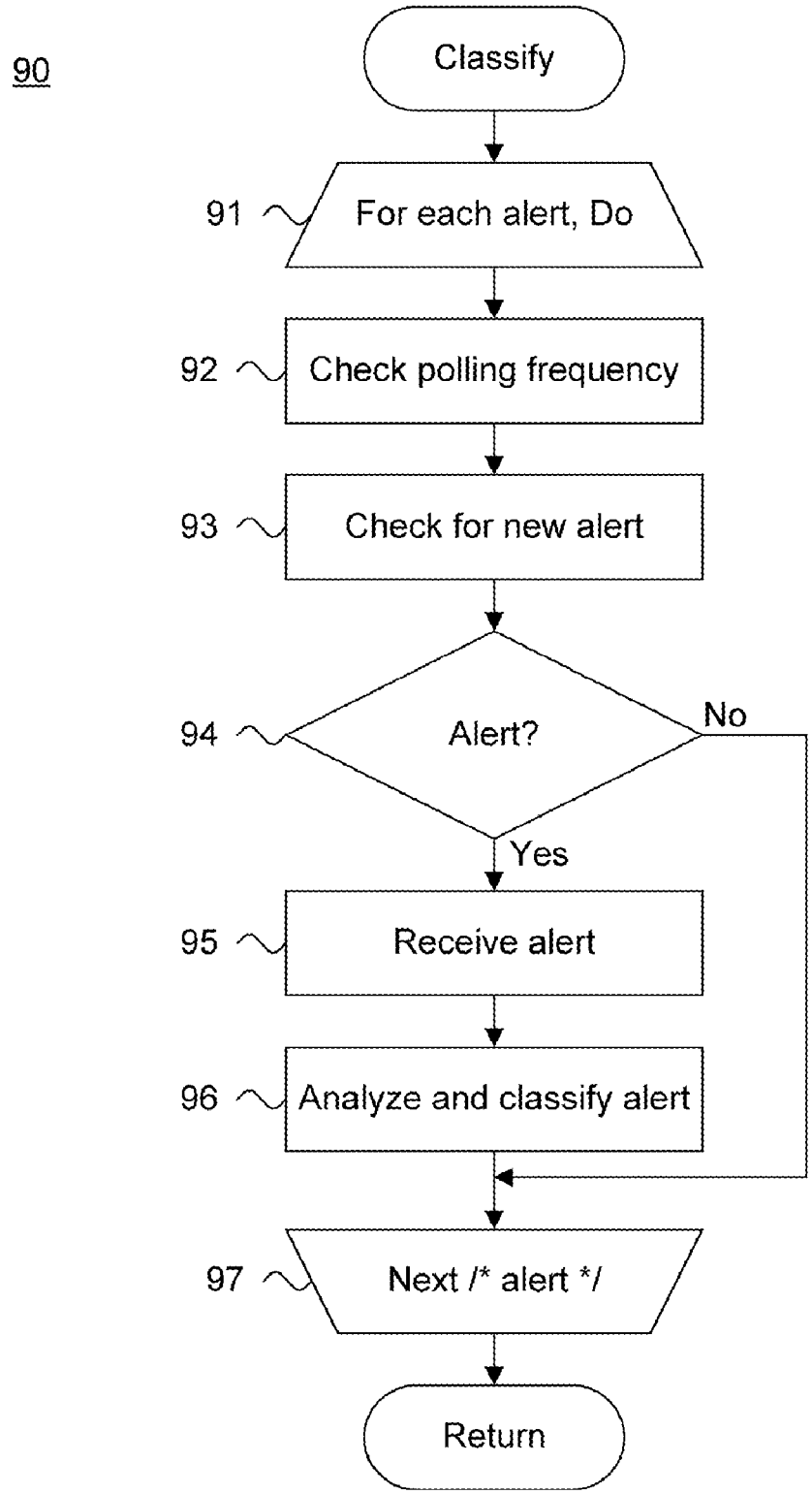
FIG. 7 is a flow diagram showing a routine for classifying alert conditions for use in the method of FIG. 6.
Figure 8:
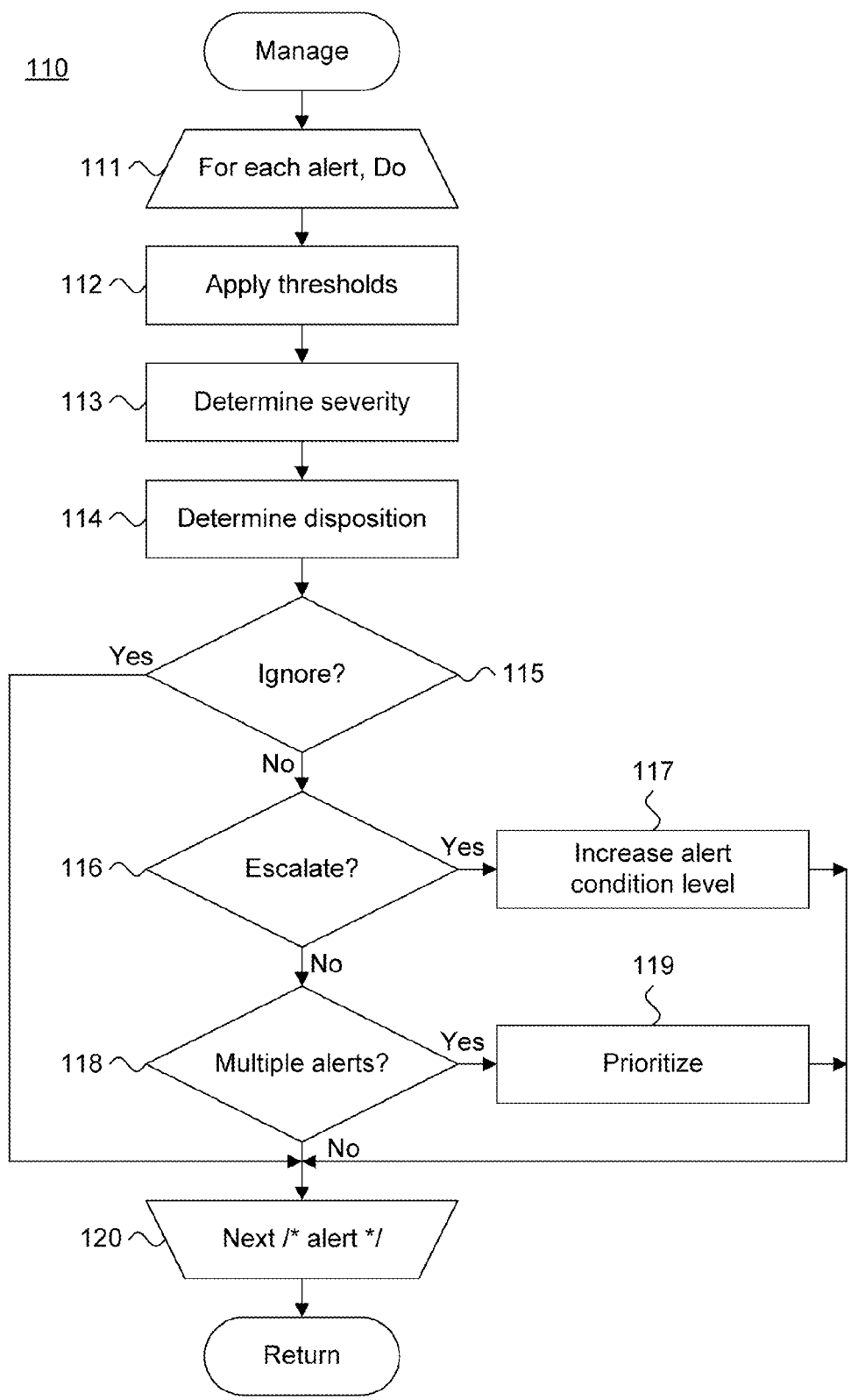
FIG. 8 is a flow diagram showing a routine for managing alert conditions for use in the method of FIG. 6.
Figure 9:
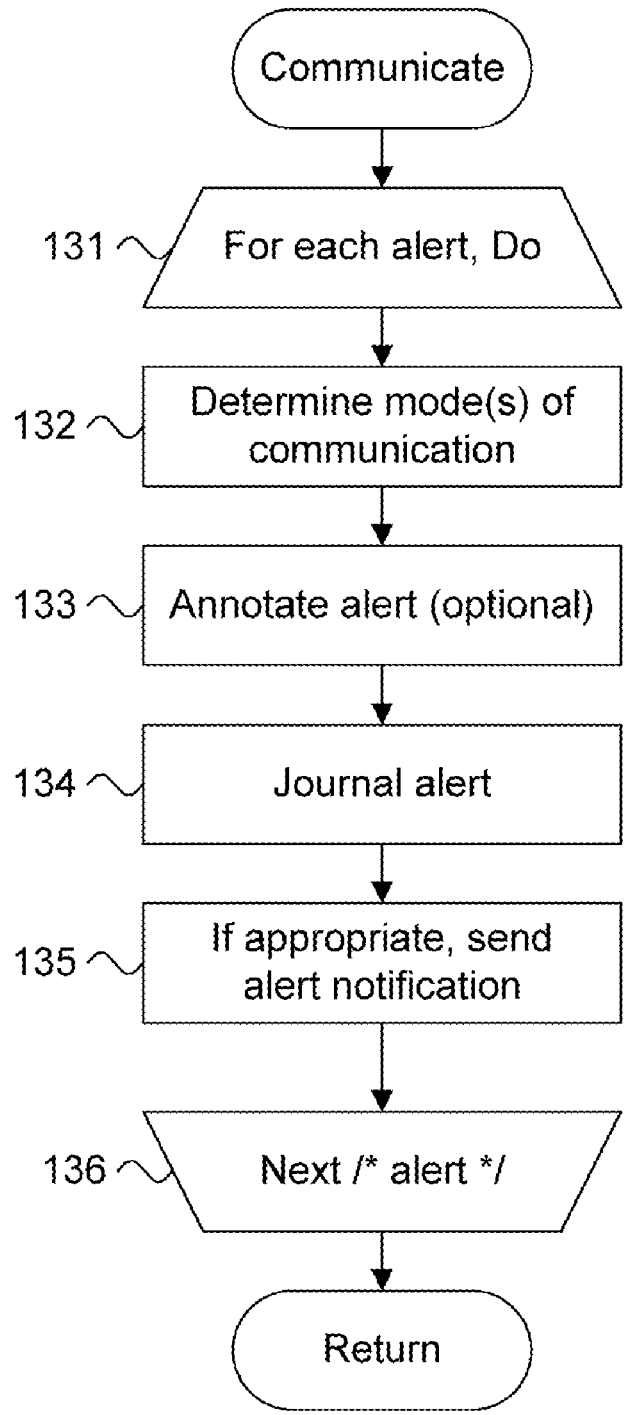
FIG. 9 is a flow diagram showing a routine for communicating alert conditions for use in the method of FIG. 6.

During each cycle (block 81), alert conditions are classified (block 82), managed (block 83), and communicated (block 84), as further described below respectively with reference to FIGS. 7, 8, and 9. Processing continues (block 85) until the processing infrastructure, for instance, the centralized server 13, terminates execution.

Classifying Alert Conditions

Alert conditions are classified based on the source or sources from which the alert condition originated. FIG. 7 is a flow diagram showing a routine 90 for classifying alert conditions for use in the method 80 of FIG. 6. Generally, the routine 90 proceeds by processing alert conditions in a continuous cycle (blocks 91-97).

During each cycle (block 91), the polling frequency associated with the current alert condition is checked (block 92) and, if appropriate, the source associated with the alert condition is checked for any new alert condition occurrences (block 93). If a new alert condition is present (block 94), the alert condition is retrieved (block 95). In a further embodiment, alert conditions are unilaterally reported by the alert condition source without requiring a specific polling request. The alert condition is then analyzed and classified (block 96). Alert condition classification assigns the alert condition into an appropriate grouping based on alert condition origination source and an analysis of potential for adverse outcome versus potential impact from medical intervention, as further described above with reference to FIG. 3. Other types of alert condition analysis and classification are possible. In a further embodiment, two or more non-alert conditions or alert conditions of nominal magnitude with non-actionable potential adverse outcome are analyzed in combination to identify potential combined alert conditions, as further described above with reference to FIG. 4. Processing continues with the next alert condition (block 97).

Managing Alert Conditions

Alert condition management provides centralized and uniform treatment of various alert conditions for a population of patients. FIG. 8 is a flow diagram showing a routine 110 for managing alert conditions for use in the method 80 of FIG. 6. Generally, the routine 110 proceeds by processing alert conditions in a continuous cycle (blocks 111-120).

During each cycle (block 111), thresholds can be applied to the alert condition (block 112) to filter out those alert conditions that do not normally require action. Similarly, the severity of the alert condition can be determined (block 113). In a further embodiment, severity levels are labeled to assist in identifying those alert conditions associated with a particular severity. Based on the severity, the disposition of the alert condition can be determined (block 114). If the disposition is not actionable, that is, the alert condition can be ignored (block 115), processing continues with the next alert condition (block 120). Otherwise, if the alert condition is pre-existing but has not been addressed and should therefore be escalated (block 116), the alert condition level is increased (block 117). Finally, if multiple alert conditions have occurred (block 118), the alert conditions are prioritized (block 119) to determine the appropriate action or actions to be taken. Processing then continues with the next alert condition (block 120).

Communicating Alert Conditions

Those alert conditions that require some form of action are communicated through alert notifications to a patient, physician, or third party, as appropriate. FIG. 9 is a flow diagram showing a routine 130 for communicating alert conditions for use in the method 80 of FIG. 6. Generally, the routine 130 proceeds by processing alert conditions in a continuous cycle (blocks 131-136).

During each cycle (block 131), the mode or modes of communication for the alert condition are determined (block 132). In one embodiment, the modes include sending the alert notification in electronic form via telephone, facsimile, e-mail, or similar means. In addition, the communication modes can include contacting individual people, such as a triage nurse, on-call physician, or medical emergency response personnel, and can include both immediate and differed delivery with verbal or written messages. Other modes of communication are possible. Optionally, the alert can be annotated (block 133) to attach notes from users, such as physicians, to add context to the alert notification process for more timely, specific, and helpful response. For example, an annotation may note that a patient has a history of not taking medications that might help in post-alert action. The alert condition is then journaled into the EMR database 24 (block 134) and, if appropriate, an alert notification is sent (block 135). Processing continues with the next alert condition (block 136).

System

Figure 10:
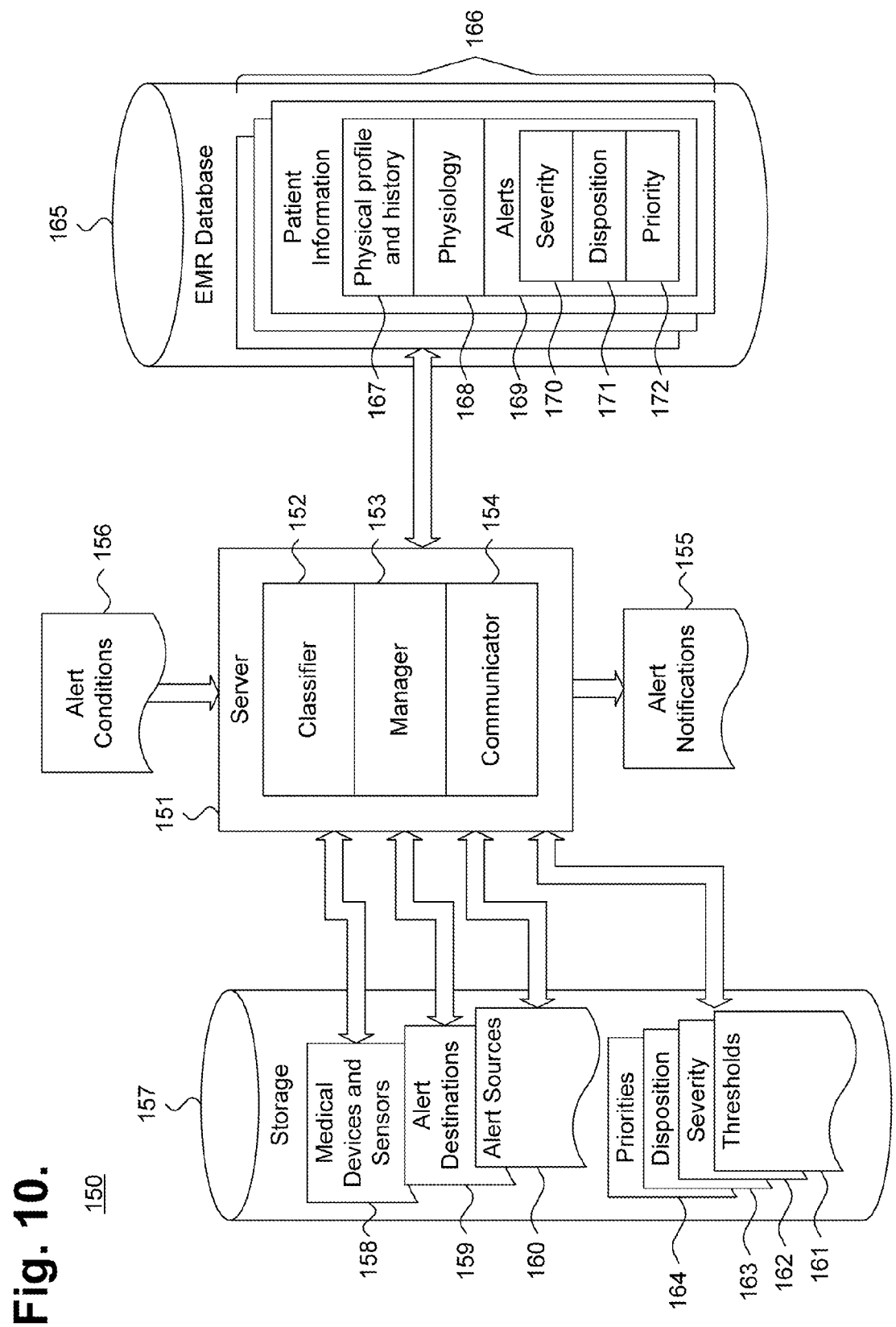
FIG. 10 is a block diagram showing a system for providing synergistic alert condition processing in an automated patient management system, in accordance with one embodiment.

Generally, the centralized server is responsible for orchestrating the processing of alert conditions for a patient population, although, in a further embodiment, the processing can be delegated to individual clients or patient management devices. FIG. 10 is a block diagram showing a system 150 for providing synergistic alert condition processing in an automated patient management system 10, in accordance with one embodiment. A server 151 implements the system 150 and executes a sequence of programmed process steps, such as described above beginning with reference to FIG. 6 et seq., implemented, for instance, on a programmed digital computer system.

The server 151 includes a classifier 152, manager 153, and communicator 154. The server 151 also maintains an interface to an EMR database 165 and storage 157. The EMR database 165 is used to maintain patient information 166, which can include physical profile and history 167, patient physiology 168, and alerts conditions 169. Each alert condition 169 includes severity 170, disposition 171, and priority 172. Other types of patient information are possible. The patient information 166 is maintained for those patients belonging to the population of patients managed by the server 151, as well as for other patients not strictly within the immediate patient population.

The storage 157 is used to maintain listings of the medical devices and sensors 158 managed by the patient management devices 12 and any programmers or similar devices 22 that can interrogate or program the medical devices or sensors 158. The storage 157 also includes a listing of alert notification destinations 159 and alert condition sources 160. Finally, the storage includes pre-determined user definitions of thresholds 161, severity 162, disposition 163, and priorities 164. Other types of device information, alert condition source, alert notification destination, and other condition management information are possible.

The classifier 152 receives incoming alert conditions 156, which are analyzed and classified into appropriate groupings for alert condition management. The manager 153 processes the alert conditions by applying the thresholds 161 and assigning severity 162 and disposition 163. As necessary, the priorities 164 are applied to resolve competing alert conditions 156.

Finally, the communicator 154 journals alert conditions into the EMR database 165 and generates alert notifications 155, as appropriate. Other components and functionality are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for alert condition management in an automated patient management system, comprising:
   a device for retrieving patient data from an origination source and evaluating the patient data for occurrence of an alert condition;
   a classifier classifying the alert condition based on the origination source and assigning the alert condition along a continuum comprising adverse outcome potential versus medical intervention impact potential;
   a manager managing the alert condition by assigning a disposition, wherein the disposition is based on relative placement of the alert condition along the continuum, severity of the alert condition, and a condition management state, wherein the condition management state is selected from the group consisting of whether the alert condition is pre-existing but has not been addressed, prioritization of the alert condition from among a plurality of alert conditions, and combinations thereof, wherein the alert condition of a pre-existing alert condition is escalated if the alert condition has not been addressed; and
   a communicator determining whether the assigned disposition is actionable and, when actionable, communicating an alert notification over a selectable mode of communication.

2. The system of claim 1, wherein the device for retrieving and evaluating patient data is proximal to the patient.

3. The system of claim 1, wherein the communicator communicates an alert notification to a remote centralized server.

4. The system of claim 1, wherein the manager applies one or more thresholds to the alert condition to determine severity.

5. The system of claim 1, wherein patient data is selected from the group consisting of device parameters, sensor readings, and health conditions.

6. The system of claim 1, wherein patient data is retrieved from a device selected from the group consisting of: implantable medical devices, external medical devices, implantable sensors, external sensors, patient management devices, personal computers, telephones, facsimile machines, and combinations thereof.

7. The system of claim 6, further comprising retrieving patient data from patient history data or a source other than an alert condition source.

8. The system of claim 1, wherein a combined alert condition is identified by evaluating a confluence of non-actionable alert conditions.

9. The system of claim 1, further comprising a monitor to monitor new alert conditions based on a scheduled polling frequency.

10. The system of claim 1, further comprising an electronic medical records database to store the alert condition prior to communicating the alert notification.

11. The system of claim 1, wherein the disposition is selected from the group consisting of recording the alert condition, sending an informational message, sending a recommendation, sending an obligatory instruction, and taking active medical interventive measures.

12. The system of claim 1, wherein the alert notification is selected from the group consisting of a telephone call, telephone message, facsimile, email, and voicemail.

13. An apparatus for providing alert condition management in an automated patient management system, comprising:
   a device for evaluating patient data from an origination source for occurrence of an alert condition;
   a classifier classifying the alert condition based on the origination source and assigning the alert condition along a continuum comprising adverse outcome potential versus medical intervention impact potential;
   a manager managing the alert condition by assigning a disposition, wherein the disposition is based on relative placement of the alert condition along the continuum, severity of the alert condition and a condition management state, wherein the condition management state is selected from the group consisting of whether the alert condition is pre-existing but has not been addressed, prioritization of the alert condition from among a plurality of alert conditions, and combinations thereof, wherein the alert condition of a pre-existing alert condition is escalated if the alert condition has not been addressed; and a communicator communicating an alert notification over a selectable mode of communications and conditioned upon the assigned disposition being actionable.

14. The apparatus of claim 13, wherein the device for retrieving and evaluating patient data is proximal to the patient.

15. The apparatus of claim 13, wherein the communicator communicates an alert notification to a remote centralized server.

16. The apparatus of claim 13, wherein the manager applies one or more thresholds to the alert condition to determine severity.

17. The apparatus of claim 13, wherein patient data is selected from the group consisting of device parameters, sensor readings, and health conditions.

18. The apparatus of claim 13, wherein patient data is retrieved from a device selected from the group consisting of: implantable medical devices, external medical devices, implantable sensors, external sensors, patient management devices, personal computers, telephones or facsimile machines.

19. The apparatus of claim 18, wherein patient data is retrieved from patient history data or a source other than an alert condition source.

* * * * *